United States Patent [19]

Sawada et al.

[11] Patent Number: 4,588,681
[45] Date of Patent: May 13, 1986

[54] PROCESS FOR PRODUCING ADULT T CELL LEUKEMIA ASSOCIATED ANTIGEN

[75] Inventors: Takashi Sawada, Yatabemachi; Tomiaki Morimoto, Hino; Isao Miyoshi; Hirokuni Taguchi, both of Kouchi; Junichi Tohmatsu, Tsuchiura; Toyohiro Kitamura, Matsudo, all of Japan

[73] Assignee: Eisai Co., Ltd., Tokyo, Japan

[21] Appl. No.: 535,457

[22] Filed: Sep. 23, 1983

[30] Foreign Application Priority Data

Sep. 30, 1982 [JP] Japan ................. 57-169670

[51] Int. Cl.$^4$ ............ C12Q 1/70; G01N 33/53; G01N 33/554; B65D 71/00

[52] U.S. Cl. ......................... 435/5; 422/61; 424/88; 435/7; 435/810; 435/948; 436/519; 436/523; 436/536; 436/542; 436/543; 436/804; 436/808; 436/811

[58] Field of Search ............ 435/7, 5, 810, 948; 424/88; 422/61; 436/519, 523, 536, 542, 543, 804, 808, 811

[56] References Cited

U.S. PATENT DOCUMENTS 4,323,555 4/1982 Theilen .................. 435/240 X

OTHER PUBLICATIONS

Robert-Guroff et al, *Detection of the Human T Cell Lymphoma Virus p19 in Cells of Some Patients with Cutaneous T Cell Lymphoma and Leukemia Using a Monoclonal Antibody*, Journal of Experimental Medicine, vol. 154, Dec. 1981, pp. 1957–1964.

Posner et al, Natural Antibodies to the Human T Cell Lymphoma Virus in Patients with Cutaneous T Cell Lymphomas, J. Exp. Med., vol. 154, Aug. 1981, p. 333–346.

Rho et al, Characterization of the Reverse Transcriptage from a New Retrovirus (HTLV) Produced by a Human Cutaneous T-Cell Line, Virology, vol. 112, pp. 355–360 (1981).

Bach, *Immunology*, title page and pp. 282–285.

Gallo et al, *HTLV: The Virus of Adult T-Cell Leukemia in Japan and Elsewhere*, The Lancet, Mar. 1982, p. 683.

Shimoyama et al, *Anti-ATLA Positive Hematologic Malignancies in the Kanto District*, Jpn. J. Clin. Oncol. 1982, 12 (1),pp. 109–116.

Yoshida et al, *Isolation and Characterization of Retrovirus from Cell Lines of Human Adult T-Cell Leukemia and its Implication in the Disease*, Proc. Natl. Acad. Sci, USA, vol. 79, Mar. 1982, pp. 2031–2035.

Miyoshi et al, *A T-Cell Line Derived from Normal Human Cord Leukocytes by Co-culturing with Human Leukemic T-Cells*, Gann, 72, Dec. 1981, pp. 978–981.

Miyoshi et al, *Type C Virus Particles in a Cord T-Cell Line Derived by Co-Cultivating Normal Human Cord Leukocytes and Human Leukaemic T Cells*, Nature, vol. 294, Dec. 1981, pp. 770–771.

Miyoshi et al, *A Novel T-Cell Line Derived from Adult T-Cell Leukemia*, Gann, 71, Feb. 1980, pp. 155–156.

Miyoshi et al, *Characteristics of a Leukemic T-Cell Line Derived from Adult T-Cell Leukemia*, Jpn. J. Clin. Oncol. 1979, 9 (Suppl.), pp. 485–493.

Hinuma et al, *Adult T-Cell Leukemia: Antigen in an ATL Cell Line and Detection of Antibodies to the Antigen in Human Sera*, Proc. Natl. Acad. Sci., USA, vol. 78, No. 10, Oct. 1981, pp. 6476–6480.

Miyoshi et al, *Asymptomatic Type C Virus Carriers in the Family of an Adult T-Cell Leukemia Patient*, Gann, 73, Apr. 1982, pp. 339–340.

Miyoshi et al, *Caution against Blood Transfusion from Donors Seropositive to Adult T-Cell Leukemia-Associated Antigens*, The Lancet, Mar. 1982, pp. 683–684.

Gallo et al, Cancer Res., 41 (1981) 4738–4739.

Polesz et al, Proc. Natl. Acad. Sci., USA, 77(1980)7415–7419.

Polesz et al, Nature, vol. 294 (1981) 268–271.

Kazyanaraman et al, J. Virology, 38(1981) 906–915.

*Primary Examiner*—Christine M. Nucker
*Attorney, Agent, or Firm*—Flynn, Thiel, Boutell & Tanis

[57] ABSTRACT

A process for producing an adult T cell leukemia associated antigen is disclosed wherein an adult T cell leukemia associated antigen producing cell is treated with a surfactant. A method for assaying adult T cell leukemia associated antibodies by enzymoimmunoassay, radioimmunoassay or passive hemagglutination is also disclosed. In this method, the adult T cell leukemia associated antigen obtained by treating the adult T cell leukemia associated antigen producing cells with a surfactant is used as the antigen in the assay procedure.

29 Claims, 1 Drawing Figure

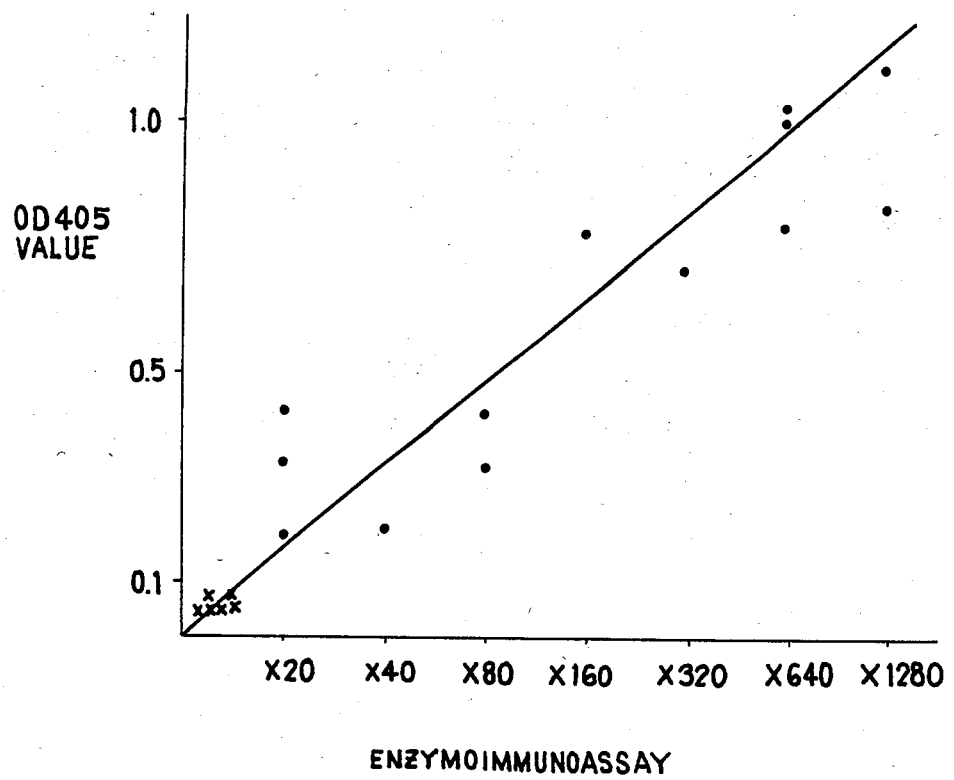

PROCESS FOR PRODUCING ADULT T CELL LEUKEMIA ASSOCIATED ANTIGEN

This invention relates to a process for producing an adult T cell leukemia associated antigen, a method for assaying an adult T cell leukemia associated antibody by use of said antigen, and a reagent used for assaying an adult T cell leukemia associated antibody comprising said antigen.

Adult T cell leukemia, or ATL, also called endemic adult leukemia/lymphoma (ATLL), is a recently identified form of leukemia described by takalsuki et al in 1977. Clinically, this disease attacks adult human beings, giving rise to a T cell having an irregular or segmented nucleus and causing lymph node enlargement, hepatomegalia or splenomegaly. In many cases, it proceeds subacutely and often is associated with skin involvement. Generally, lymphatic leukemia affects infant human beings, but it is mostly of a non-T, non-B type. Adult T cell leukemia exclusively affects adults and is typified by morbid cells having the surface character of a peripheral T cell.

The incidence distribution of adult T cell leukemia in Japan is evidently biased to certain localities. This disease has a tendency to occur in Kyushu and Southern Shikoku, and it is reported that many patients who began suffering from this disease in Tokyo or Osaka came from the Kyushu or Shikoku districts. As mentioned below, it is known that this disease is caused by the infection of a virus associated with this disease, the so-called adult T cell leukemia virus, hereinafter referred to as ATLV. It is thus possible to determine a local distribution of antibody-positive persons by detecting the adult T cell leukemia associated antibody which develops in persons who become infected with the virus.

The results of a previous investigation show that patients afflicted with this disease are found mostly in Kyushu and Shikoku and also are distributed throughout Okinawa and the Kii Peninsula. It was further found that this disease follows certain specified family lines, which suggests that familial transmission of this disease is likely.

ATLV is a pathogen for adult T cell leukemia. This finding stems from the success of one of the present inventors in cultivating an adult T cell leukemia cell strain, designated MT-1 cells, from the peripheral blood of an adult T cell leukemic patient. As a result of a joint study by this inventor and other researchers, it was found that an antigen exists which specifically reacts with and is intimately associated with adult T cell leukemic serum and C-type viral particles or virions. This antigen was tentatively named the "adult T cell leukemia associated antigen (ATLA)".

The following literature references give details about these findings: Miyoshi, I. et al: Gann, 71:155, 1980; Miyoshi, I. et al: Jap. J. Clin. Oncol., 9 (Suppl.): 485, 1979; and Hinuma, Y. et al: Proc. Nat. Acad. Sci., 78:6476, 1981.

Almost at the same time as the discovery of ATLA, Gallo et al in the United States succeeded in deriving a T cell strain from mycosis fungoides and Sézary syndrome patients by using a T cell growth promoting factor, and disclosed their discovery of a C-type retrovirus (HTLV) in the cultured cells. Mycosis fungoides, Sézary syndrome and adult T cell leukemia are diseases which are clinically akin to each other, and the fact that a C-type virus was found in the cultured cells of Gallo et al suggests the possibility that this virus could be an etiological factor in certain kinds of T cell associated tumors in man.

As described above, it has been shown that ATLV is a pathogen of adult T cell leukemia. The mechanism of transmission of ATLV is still not completely understood, but in view of the fact that many antibody-positive persons are found in the same family and that the antibody positiveness ratio is high among married couples, it is considered probable that the disease is transmitted from mother to child through fetation, parturition or breast feeding, or is transmitted by horizontal transmission due to physical contact between married couples. In connection with such transmission, regarding the prevention of the infection, one of the present inventors has previously verified that some adult T cell leukemia associated antibody-positive persons are blood transfusion donors, and such donors could carry ATLV. That is, there is a possibility that blood transfusions could play a very important role in the transmission of ATLV. Also, the fact that adult T cell leukemia associated antibody-positive persons are found among persons who have received blood transfusions frequently in connection with diseases other than adult T cell leukemia suggests the possibility that ATLV is transmitted through blood transfusion. The following literature references disclose findings verifying or relating to these facts: Miyoshi, I. et al: Gann, 73:339, 1982; Miyoshi, I. et al: Lancet: 683, 1982; and Shimoyama, M. et al: Jap. J. Clin. Oncol., 12:109, 1982.

Under these circumstances, urgent measures need to be taken to check whether a blood donor carries adult T cell leukemia associated antibodies and to thereby prevent the infection of blood transfusion recipients with ATLV from such an antibody-positive person. For this purpose, it is essential that a method for assaying adult T cell leukemia associated antibodies, with high sensitivity, be established, and that a method be achieved for high-yield production of an adult T cell leukemia associated antigen, especially a highly active one, which is needed for the practice of such an assay. A reagent which can be prepared in advance for facilitating the practice of this assay is also desired.

In the prior art, a method is known for assaying adult T cell leukemia associated antibodies by an indirect fluorescent antibody technique. According to this method, MT-1 or MT-2 cells, which are adult T cell leukemia associated antigen producing cells, are smeared, air-dried and acetone-fixed on a glass slide, and then a specimen serum is reacted therewith. This method, however, requires special apparatus, requires that the person carrying out the test have a great deal of skill, is incapable of treating a large number of specimens at one time, and is also poor in detection sensitivity.

BRIEF DESCRIPTION OF THE DRAWING

The drawing is a graph showing the relationship between the fluorescent antibody titer determined by the indirect fluorescent antibody method and the $OD_{405}$ value determined by enzymoimmunoassay according to this invention, based on the results obtained in Test Example 2.

Under these circumstances, the present inventors have conducted extensive research, and as a result, have found that a practical method for assaying adult T cell leukemia antibodies can be attained. According to this invention, an adult T cell leukemia associated antigen is produced by treating adult T cell leukemia associated antigen producing cells with a surfactant, and then performing enzymoimmunoassay, radioimmunoassay or passive hemagglutination on a blood serum sample from a subject, using this antigen as a test reagent. The results of any one of these tests will reveal, with a high degree of sensitivity, whether or not adult T cell leukemia antibodies are present in the blood of the subject. The present invention was achieved on the basis of these findings.

Thus, an object of this invention is to provide a method capable of assaying adult T cell leukemia associated antibodies with high sensitivity. A further object of the invention is to provide a method for producing an adult T cell leukemia associated antigen necessary for the practice of the assay method of the invention, which antigen is highly active and is produced in a high yield. An additional object of the invention is to provide an assay reagent which can be prepared in advance and which allows the assay to be easily practiced. In order to accomplish these objects, the invention comprises, as its essential steps, treating adult T cell leukemia associated antigen producing cells with a surfactant to extract the adult T cell leukemia associated antigen from the cells, and then performing an immunoassay which can be enzymoimmunoassay, radioimmunoassay or passive hemagglutination, of a blood serum sample from a subject using the thus-obtained adult T cell leukemia associated antigen. In the context of the present invention, the term "immunoassay" refers only to the three techniques of enzymoimmunoassay, radioimmunoassay, or passive hemagglutination.

The invention will now be described in detail.

The term "adult T cell leukemia associated antigen" is used herein to refer to antigenic proteins and C-type virions present in a culture of leukemia cells collected from the peripheral blood of an adult T cell leukemic patient and typified by a specific antibody-antigen reaction with adult T cell leukemia antibodies in adult T cell leukemic blood serum. The antigenic protein is composed of a plurality of proteins having different molecular weights, principally proteins having a molecular weight of about 24,000. The term "C-type virion" refers to an RNA virion having reverse transcriptase activity. Its shape is spherical, as viewed under an electron microscope, and its density, as measured by the sucrose gradient centrifugation method, is 1.152 to 1.155 g/cm$^3$. Further particulars, including the properties of the adult T cell leukemia associated antigen, are disclosed in an article by Yoshida, M. et al: Proc. Nat. Acad. Sci., 79:2031, 1982, the entire contents of which are expressly incorporated by reference herein.

The adult T cell leukemia associated antigen according to this invention, can be obtained by treating an adult T cell leukemia associated antigen producing cell with a surfactant. Its characteristic properties are the same as the properties of the antigen described by Yoshida et al as mentioned above. Thus, the adult T cell leukemia associated antigen according to this invention is unique in that it is obtained by a specified treatment of selected adult T cell leukemia associated antigen producing cells, but the antigen itself is the same as the adult T cell leukemia associated antigen defined above.

The term "adult T cell leukemia associated antigen producing cell" as used herein includes all cell strains that can produce the above-defined adult T cell leukemia associated antigen. Cells which fall in this class and which are presently available include cells of a series of cultured cell strains generally identified as MT-1, MT-2, MT-3 and MT-4 cells. These cultured cell strains have been established and available methods for obtaining these cells have been previously published by one of the present inventors. It was found that among them, the MT-2 cells are the most advantageous from the viewpoint of mass production. MT-2 cells are thus used as the adult T cell leukemia associated antigen producing cells in the example described in detail below.

MT-2 cells are a cell strain derived from umbilical cord leukocytes obtained from a mixed culture of leukemia cells of an adult T cell leukemic human female patient and umbilical cord leukocytes of a normal, non-leukemic, human male neonate. The chromosome number of MT-2 cells is 46 (XY). An MT-2 cell is considered to result from transduction of an adult T cell leukocyte virus genome from a leukocyte cell of the patient into an umbilical cord leukocyte T cell of the neonate. MT-2 cells grow to form a cluster, form a rosette with sheep red blood cells and react with monoclonal antibodies specific to the T cells. MT-2 cells are also negative to EB virus nucleus antigen. The following literature references further describe the properties and methods of obtaining MT-2 cells: Miyoshi, I. et al: Gann, 72:978, 1981 and Miyoshi, I et al: Nature, 294:770, 1981, the entire contents of both of which are expressly incorporated by reference herein.

As the surfactant used in this invention, sodium deoxycholate, octylphenoxypolyethoxyethanol and polyoxyethylene (10) octylphenyl ether can be employed. The present invention contemplates the use of other surfactants with similar properties and is by no means confined to these examples. The preferred surfactant concentration in the method of this invention is about 0.2 wt. %, and for this purpose it is possible to use, for example, a veronal buffer containing 0.2 wt. % of sodium deoxycholate (pH 7.5, $\mu$=0.145). In practice, it is preferred that about 5 ml of this buffer having the abovedefined concentration be added per from $10^7$ to $10^8$ of the MT-2 cells. These amounts merely illustrate a preferred embodiment of the invention and do not restrict the scope of the invention. Other concentration ranges may be employed in order to achieve the objects of the invention.

The treatment of MT-2 cells with a surfactant in this invention is conducted, for example, as follows.

First, a 0.15M phosphate-buffered saline solution (pH 7.2) is added to wash from $10^7$ to $10^8$ MT-2 cells, and the washed cells are then centrifuged and packed. Then, 5 ml of a 0.2 wt. % sodium deoxycholatecontaining veronal buffer (pH 7.5, $\mu$=0.145) is added to the MT-2 cells and the mixture is stirred at, for example, 4° C. for 4 hours. The mixture is then centrifuged and the supernatant is removed, poured in a dialysis tube and dialyzed with a 0.15M phosphatebuffered saline solution (pH 7.2) at, for example, 4° C. for 2 days. This dialysis is conducted for the purpose of removing the surfactant contained in the supernatant. After dialysis, the solution is centrifuged and the supernatant is removed. This supernatant contains the adult T cell leukemia associated antigen according to this invention.

As described above, the essential purpose of the method of the invention is to subject an adult T cell leukemia associated antigen producing cell to a treatment with a surfactant under stirring. The procedures carried out before and after this surfactant treatment, such as washing and dialysis, should be appropriately performed so that the objects of the invention can be achieved.

An embodiment of the assay method of this invention will now be described.

The adult T cell leukemia associated antibody induces a specific antigen-antibody reaction with an adult T cell leukemia associated antigen according to this invention. More specifically, such antibodies are contained in the specimen blood serum which is to be treated in the process of this invention.

The assay step of the method of this invention utilizes the known techniques of enzymoimmunoassay, radioimmunoassay or passive hemagglutination. The procedures for these immunoassay methods are commonly known. The method of this invention will be described below for an embodiment wherein the enzymoimmunoassay technique is utilized.

The assay system according to the enzymoimmunoassay procedure, as applied in the present invention, consists essentially of a solid phase, an adult T cell leukemia associated antigen according to this invention, adult T cell leukemia associated antibodies present in the test serum, anti-human IgG antibodies (labelling antibodies), an enzyme and a substrate. As the solid phase, a microtiter plate cup or glass beads specifically prepared for enzymoimmunoassay can be used. Before commencing the assay, an adult T cell leukemia associated antigen, according to this invention, is dissolved in a 0.15M phosphate-buffered saline solution and the solution is put into, for example, a polystyrene enzymoimmunoassay cup and left at 4° C. for one hour, whereby the surface of the solid phase becomes coated with the adult T cell leukemia associated antigen, according to this invention. The test serum containing the adult T cell leukemia associated antibodies can be added, as is, to the assay system, but preferably it is diluted, for example, to 1/100 its initial concentration with normal rabbit serum (NRS).

As the anti-human IgG antibodies, which are the labelling antibodies, for example, goat anti-human IgG antibodies or mouse anti-human Fc monoclonal antibodies can be used. As the enzyme, there can be used, for example, alkali phosphatase, glucose oxidase, peroxidase, or beta galactosidase. Before the assay is conducted, the enzyme can be conjugated to the labelling antibody with a conjugating agent, such as glutaraldehyde, to prepare in advance part of the reagent used in the assay method of the invention.

The substrate is selected according to the type of the enzyme used. For instance, when alkali phosphatase is used as the enzyme, p-nitrophenyl phosphate or the like can be used as the substrate. Among the foregoing component elements of the assay system, the use of the recited elements other than the adult T cell leukemia associated antigen according to this invention and the test serum is preferred but is not critical to the process of this invention.

The assay can be carried out according to the conventional enzymoimmunoassay procedure. For instance, as will be discussed in the Examples which follow, a test serum is first put into a cup, the interior of which is coated with an adult T cell leukemia associated antigen, according to this invention, and the mixture is incubated. Then, an enzyme-labelled antibody such as goat anti-human IgG-alkali phosphatase conjugate is added and the resulting mixture is incubated. Finally, a substrate such as p-nitrophenyl phosphate is added and the mixture is further incubated, after which the amount of the substrate decomposed is measured with a spectrophotometer. Measurement of the amount of substrate decomposed allows determination of the level of adult T cell leukemia associated antibodies by routine calculation.

The results of this assay procedure, according to the process of this invention, correlate well with results obtained according to the indirect fluorescent antibody technique which has been conventionally used for the assay of the adult T cell leukemia associated antibodies. As shown by the Test Examples given below, the results obtained according to enzymoimmunoassay in the present invention correlate with results obtained according to the indirect fluorescent antibody method in discriminating between an antibody-positive person and a normal person, and in the determination of the amount of adult T cell leukemia associated antibodies present. The assay method of this invention is far superior to the indirect fluorescent antibody method in assay sensitivity, the method of the invention being at least 16 times higher in sensitivity than the indirect fluorescent antibody method. Thus, the process of this invention is capable of assaying adult T cell leukemia associated antibodies with high sensitivity.

In summary, the reagent used in this invention contains an adult T cell leukemia associated antigen according to this invention as an essential constituent. The assay method using this reagent according to this invention utilizes the known techniques of enzymoimmunoassay, radioimmunoassay or passive hemagglutination. For instance, when the enzymoimmunoassay technique is used, the reagent of this invention is embodied as follows. The assay reagent of this invention is either an adult T cell leukemia associated antigen provided according to this invention or said antigen combined with one or more materials selected from a solid phase, a labelling antibody, an enzyme and a substrate as discussed above. If a solid phase is included, the solid phase can be coated with the adult T cell leukemia associated antigen according to this invention. If a labelling antibody and an enzyme are used, they can be added to the mixture as a conjugate, that is, as a labelled antibody. The reagent of this invention can be formulated in all of the foregoing ways. A suitable buffer solution, a normal rabbit serum (NRS) or other substances that can facilitate the assaying operation in the process of this invention, can also be incorporated into the reagent mixture. The use of these additives does not restrict the scope of the invention.

The effects of this invention are shown by the following Test Examples.

Test Example 1

Specimens:
The following specimens (1) to (5) were prepared:

| | |
|---|---|
| Specimen (1): (Comparison) | $2 \times 10^7$ MT-2 cells were homogenized at 4° C. for one minute and then centrifuged at 10,000 rpm for 20 minutes, and the supernatant was removed for use as specimen (1). |
| Specimen (2): (Comparison) | $2 \times 10^7$ MT-2 cells were frozen and thawed three times in succession and then centrifuged at 10,000 rpm for 20 minutes, and the supernatant was removed for use as specimen (2). |
| Specimen (3): (Invention) | 5 ml of 0.2 wt. % polyoxyethylene (10) octylphenyl ether was added to $2 \times 10^7$ MT-2 cells and the solution was |

-continued

| Specimen | Description |
|---|---|
| | stirred at 4° C. for 3 hours and then centrifuged at 10,000 rpm for 20 minutes, and the supernatant was dialyzed with a 0.15M phosphate-buffered saline solution at 4° C. for 2 days. The resulting solution was again centrifuged at 10,000 rpm for 20 minutes and the supernatant was removed for use as specimen (3). |
| Specimen (4): (Invention) | The same procedure as used for the preparation of specimen (3) was followed except that 0.2 wt. % octylphenoxypoly-ethoxyethanol was used instead of 0.2 wt. % polyoxyethylene (10) octylphenyl ether to prepare specimen (4). |
| Specimen (5): (Invention) | The same procedure as used for the preparation of specimen 3 was followed except that 0.2 wt. % sodium deoxycholate was used instead of 0.2 wt. % polyoxy-ethylene (10) octylphenyl ether to prepare specimen (5). |

Method:

The $OD_{280}$ value of each specimen was measured to determine the protein content of the specimen, and then each specimen was subjected to an Ouchterlony test with a high-titer patient serum containing adult T cell leukemia associated antibodies.

Results:

The results are given in Table 1.

TABLE 1

| Specimen | Protein level ($OD_{280}$/ml) | Antigenic activity (Ouchterlony test with high-titer patient serum) |
|---|---|---|
| (1) (Comparison) | 11 | — |
| (2) (Comparison) | 13 | — |
| (3) (Invention) | 25 | + |
| (4) (Invention) | 28 | + |
| (5) (Invention) | 38 | + |

In the Ouchterlony test results given in the above table, a "—" sign indicates that no clear formation of a precipitin curve was observed, and a "+" sign indicates that formation of such a curve was recognized.

Table 1 shows that the process of this invention, as compared with the conventional method, is capable of producing an adult T cell leukemia associated antigen of such a high activity that a reaction is evident even in the Ouchterlony test, and that this antigen can be produced in a high yield.

Test Example 2

Specimens:

Samples of 13 blood sera from adult T cell leukemia associated antibody-positive persons and 6 blood sera from normal persons were used as specimens. The 6 blood sera from normal persons were confirmed to be negative to adult T cell leukemia associated antibodies by the indirect fluorescent antibody method.

Method:

Each specimen was assayed by the indirect fluorescent antibody method described below and by the enzymoimmunoassay method according to this invention.

Indirect fluorescent antibody method:

MT-2 cells were smeared on a slide to form a preparation and air-dried at room temperature. A test serum diluted by 10 times with a phosphate-buffered saline solution was then added to the MT-2 cells. The resulting solution was left standing at 37° C. for 30 minutes, and then the preparation was washed three times with phosphate-buffered saline solution, to which was then added FITC (fluorescein isothiocyanate)-labelled anti-human IgG antibodies. The thus-treated preparation was left standing at 37° C. for 30 minutes, then washed three times with phosphate-buffered saline solution and observed under a fluorescent microscope through a cover glass.

Enzymoimmunoassay:

The supernatant containing the adult T cell leukemia associated antigen of this invention obtained in Example 1 below was diluted with a 0.15M phosphate-buffered saline solution so that the $OD_{280}$ value became 0.4, and 150 µl of this diluted supernatant was put into several polystyrene enzymoimmunoassay cups. Each cup was left standing at 4° C. for one hour, then washed with deionized water, and 100 µl of test serum diluted by 100 times with NRS, so that the concentration of the test serum was 1/100 of the original serum concentration, was added thereto. Each cup was again left standing at 4° C. for one hour and then washed with deionized water. Then, 100 µl of an anti-human IgG-alkali phosphatase conjugate diluted to an optimum concentration with 25% NRS was added to each cup. After allowing the resulting mixtures to stand for one hour at 37° C., the contents of each cup were washed with deionized water, and 100 µl of a substrate prepared by dissolving p-nitrophenyl phosphate in a carbonate buffer (pH 9.5, 4mM $MgCl_2$) to a concentration of 4 mg/ml was added thereto. After allowing the mixture to stand for one additional hour at 37° C., 100 µl of 1N NaOH was added to stop the reaction, and the absorbance at 405 nm ($OD_{405}$ value) was measured.

Results:

The results are shown in the drawing, which is a graph showing the relationship between the results of the assay by the indirect fluorescent antibody technique and the results determined by the enzymoimmunoassay method. In this graph, the titer determined by the indirect fluorescent antibody method, the fluorescent antibody titer, is plotted as the abscissa, and the $OD_{405}$ value determined by the enzymoimmunoassay according to the process of this invention is plotted as the ordinate. In the graph, points plotted with an "x" refer to the results obtained for the blood sera of normal persons, and points plotted with a solid dot refer to results for the blood sera of the adult T cell leukemia associated antibody-positive persons. The graph indicates the following conclusions:

(1) The assay results from the indirect fluorescent antibody method and those from the enzymoimmunoassay according to this invention correlate with each other.

(2) If a serum having a fluorescent antibody titer of x20 is diluted 320 times and is assayed, the indirect fluorescent antibody method gives a vague result, but when the same diluted serum is assayed by the enzymoimmunoassay method of this invention, it can be judged as positive. Thus, the method of this invention is at least 16 times higher in sensitivity than the conventional indirect fluorescent antibody method.

(3) The method of this invention is capable of discriminating between adult T cell leukemia associated antibody-positive persons and normal persons. The present invention will be described in further detail by the following examples.

EXAMPLE 1

A 0.15M phosphate-buffered saline solution (pH 7.2) was added to $2.4 \times 10^7$ MT-2 cells, the resulting mixture was centrifuged, and the thus-treated cells were packed. Then, 5 ml of a veronal buffer (pH 7.5, $\mu = 0.145$) containing 0.2 wt. % of sodium deoxycholate was added to the packed cells, and the resulting mixture was stirred at 4° C. for 4 hours and then centrifuged at 10,000 rpm for 30 minutes. The supernatant was then removed, packed into a dialysis tube, dialyzed against a 0.15M phosphate-buffered saline solution at 4° C. for 2 days, then centrifuged for 30 minutes at 10,000 rpm, and then the resulting supernatant was collected, thereby obtaining a supernatant containing an adult T cell leukemia associated antigen according to this invention. The $OD_{280}$ value of this supernatant was 15/ml.

EXAMPLE 2

The adult T cell leukemia associated antigen containing supernatant obtained in Example 1 was diluted by adding a 0.15M phosphate-buffered saline solution thereto so that the $OD_{280}$ value became 0.4, and 150 μl of the diluted supernatant was put into each of several polystyrene enzymoimmunoassay cups. After each solution was allowed to stand for one hour at 4° C., the solutions were removed from the cups and each cup was washed with deionized water. In each of the thus-prepared cups was set a combination of goat anti-human IgG antibody-alkali phosphatase conjugate and p-nitrophenyl phosphate. This set of ingredients served as a reagent in the assay process utilizing the enzymoimmunoassay technique. For convenience of the assay operation, a normal rabbit serum (NRS) and a 0.05M carbonate buffer (pH 9.5, 4mM $MgCl_2$) were also added into the mixture.

EXAMPLE 3

Samples of goat anti-human IgG antibodies and mouse anti-human IgG (Fc) antibodies were dissolved in a 0.05 phosphate buffer (pH 7.5), and the protein concentration was adjusted to 1 mg/ml. To 10 μl of this solution was added 50 μl of $^{125}$I-Na of 1 mCi, followed by further addition of 10 μl of a solution formed by dissolving chloramine T in a further quantity of said phosphate buffer in an amount of 1.5 mg/ml, and the mixed solution was stirred for 30 seconds. Then, 100 μl of a solution formed by dissolving sodium metabisulfite in a further quantity of said phosphate buffer in an amount of 2 mg/ml was added to stop the reaction. To this reaction solution was added 100 μl of a solution prepared by dissolving potassium iodide in a further quantity of said phosphate buffer in an amount of 10 mg/ml, and immediately thereafter, this solution was subjected to Sephadex G-50 gel filtration to separate the $^{125}$I-labelled substance and $^{125}$I. The $^{125}$I-labelled substance obtained showed a specific activity of about 5 to 20μ Ci/μg.

This $^{125}$I-labelled substance was suitable for use as a radioimmunoassay reagent.

EXAMPLE 4

Sheep blood was poured into a centrifuge tube and centrifuged 5 times in succession at 2,000 rpm for 10 minutes each time using a physiological saline solution to wash the erythrocytes. A 0.15M phosphate-buffered saline solution of pH 7.5 was added to these erythrocytes to adjust the amount of erythrocytes to 5 wt. %.

To this erythrocyte suspension was added 20% by volume of a glutaraldehyde solution adjusted to a concentration of 2.5 wt. % with a further amount of said phosphate-buffered saline solution, and the resulting mixture was reacted under stirring at room temperature for about 5 hours to fix the erythrocytes. This solution was then centrifuged to obtain the fixed erythrocytes and the latter were washed several times by centrifugation using a saline solution. A further amount of said phosphate-buffered saline solution was added to these fixed erythrocytes to form a suspension containing 5 wt. % of the fixed erythrocytes, and to this suspension was added an equal amount of a tannic acid solution adjusted to 5 mg/dl with a further quantity of said phosphate-buffered saline solution. The mixed solution was then stirred for 30 minutes. This solution was centrifuged to obtain tannic acid-treated fixed erythrocytes, and the latter were further washed several times by centrifugation using a saline solution. To the thus-obtained tannic acid-treated fixed erythrocytes was added a further quantity of said phosphate buffer saline solution to prepare a suspension containing 5 wt. % of the acid-treated fixed erythrocytes.

This erythrocyte suspension was mixed with an equal amount of a solution prepared by diluting an adult T cell leukemia associated antigen of this invention with a further quantity of said phosphate-buffered saline solution to a protein concentration of about 5 mg/ml, and the mixture was stirred at room temperature for 60 minutes to effect sensitization. This solution was centrifuged to obtain sensitized erythrocytes, and the latter were further washed several times by centrifugation using a saline solution. To the thus-obtained sensitized erythrocytes was added a further quantity of said phosphate-buffered saline solution containing 2% of normal rabbit serum to prepare a 7 wt. % suspension. This sensitized erythrocyte suspension was suitable for use as an assay reagent in the embodiment of this invention utilizing the passive hemagglutination technique.

The embodiments of the invention in which an exclusive property of privilege is claimed are defined as follows:

1. A process for producing an antigen associated with adult T cell leukemia which comprises treating adult T cell leukemia associated antigen producing cells with a surfactant capable of separating said antigen from said cells and selected from group consisting of sodium deoxycholate, octylphenoxypolyethoxyethanol and polyoxyethylene (10) octylphenyl ether, and then recovering said antigen.

2. A process as claimed in claim 1 wherein said surfactant is sodium deoxycholate.

3. A process as claimed in claim 1 wherein said adult T cell leukemia associated antigen producing cells are MT-2 cells.

4. A process as claimed in claim 2 wherein said adult T cells leukemia associated antigen producing cells are MT-2 cells.

5. A process for the preparation of an antigen associated with adult T cell leukemia, which comprises:
providing adult T cell leukemia associated antigen producing cells, said antigen comprising antigenic proteins associated with adult T cell leukemia and C-type virions associated with adult T cell leukemia;
then adding a surfactant selected from the group consisting of sodium deoxycholate, octylphenoxypolyethoxyethanol and polyoxyethylene (10) octylphenyl ether to said cells in an aqueous medium to form a mixture whereby to separate said antigen from said cells;
then removing said antigen from said mixture.

6. A process as claimed in claim 5, wherein said adult T cell leukemia associated antigen producing cells are MT-2 cells.

7. A process as claimed in claim 5, further comprising the steps of stirring said mixture before removing said surfactant, then dialyzing said mixture in order to remove said surfactant from said mixture, then centrifuging said mixture to obtain a supernatant liquid containing said antigen.

8. A process as claimed in claim 7, wherein said aqueous medium is a phosphate-buffered saline solution.

9. A method for assaying adult T cell leukemia associated antibodies by immunoassay, wherein the improvement comprises assaying a blood serum sample derived from a human subject by contacting said blood serum sample, under conditions effective to induce an antigen-antibody reaction, with an adult cell leukemia associated antigen obtained by treating adult T cell leukemia associated antigen producing cells with a surfactant capable of separating said antigen from said cells and selected from the group consisting of sodium deoxycholate, octylphenoxypolyethoxyethanol and polyoxyethylene (10) octylphenyl ether and recovering said antigen therefrom, and thereby determining whether adult T cell leukemia associated antibodies are present in said serum sample.

10. A method as claimed in claim 9, wherein said surfactant is sodium deoxycholate.

11. A method as claimed in claim 9, wherein said adult T cell leukemia associated antigen producing cells are MT-2 cells.

12. A method for assaying adult T cell leukemia associated antibodies which comprises:
providing adult T cell leukemia associated antigen producing cells, said antigen comprising antigenic proteins associated with adult T cell leukemia and C-type virions associated with adult T cell leukemia;
then adding a surfactant selected from the group consisting of sodium deoxycholate, octylphenoxypolyethoxyethanol, and polyoxyethylene (10) octylphenyl ether to said cells in an aqueous medium to form a mixture;
then removing said antigen from said mixture;
then immunoassaying a blood serum sample derived from a human subject by contacting said blood serum sample with said adult T cell leukemia associated antigen under conditions effective to induce an antigen-antibody reaction, and thereby determining the content of adult T cell leukemia associated antibodies present in said serum sample.

13. A method as claimed in claim 13, wherein said step of immunoassaying said serum sample is performed by enzymoimmunoassay.

14. A method as claimed in claim 12, wherein said step of immunoassaying said serum sample is performed by radioimmunoassay.

15. A method as claimed in claim 12, wherein said step of immunoassaying said serum sample is performed by passive hemagglutination.

16. A method as claimed in claim 12, wherein said cells are MT-2 cells.

17. A method as claimed in claim 13, further comprising performing said enzymoimmunoassay by the steps of:
adding said antigen to said blood serum sample;
adding enzyme-labeled anti-human IgG antibodies to said sample;
then incubating said sample;
then adding a substrate capable of being decomposed by said enzyme to said sample;
then further incubating said sample;
then measuring the amount of substrate decomposed in said sample; and
determining the amount of adult T-cell leukemia antibodies present in said sample based on said amount of said substrate decomposed.

18. A reagent kit adapted for use in assaying adult T cell leukemia associated antibodies by immunoassay, comprising a first package containing an adult T cell leukemia associated antigen obtained by the process as claimed in claim 1 and a separate second package containing an immunoassay composition capable of indicating the reaction of said antigen with adult T cell leukemia associated antibodies.

19. A reagent kit as claimed in claim 18, wherein said surfactant is sodium deoxycholate.

20. A reagent kit as claimed in claim 18 wherein said cells are MT-2 cells.

21. A reagent kit as claimed in claim 19 wherein said cells are MT-2 cells.

22. A reagent kit adapted for use in assaying adult T cell leukemia associated antibodies by immunoassay, comprising a first package containing an adult T cell leukemia associated antigen obtained by the process as claimed in claim 5 and a separate second package containing an immunoassay composition capable of indicating the reaction of said antigen with adult T cell leukemia associated antibodies.

23. A reagent kit as claimed in claim 18, wherein said first package comprises erythrocytes suitable for use in passive hemagglutination which have been sensitized with said antigen.

24. A reagent kit as claimed in claim 18, wherein said second package includes a substance containing radioactive labeling molecules, said substance being suitable for use in radioimmunoassay of adult T-cell leukemia associated antibodies.

25. A reagent kit as claimed in claim 18, wherein said second package immunoassay composition comprises a conjugate of an enzyme and an immunoglobulin suitable for use in enzymoimmunoassay of adult T-cell leukemia associated antibodies and a substrate capable of reacting with said enzyme.

26. A reagent kit as claimed in claim 25, wherein said conjugate is antihuman IgG-alkali phosphatase conjugate, and said substrate is p-nitrophenyl phosphate.

27. A composition from which an adult T cell leukemia associated antigen can be isolated which comprises a mixture of adult T cell leukemia associated antigen producing cells and a surfactant capable of separating said antigen from said cells and selected from the group consisting of sodium deoxycholate, octylphenoxypolyethoxyethanol and polyoxyethylene (10) octylphenyl ether, in an aqueous medium.

28. A composition as claimed in claim 27, wherein said cells are MT-2 cells.

29. A composition as claimed in claim 27, wherein said surfactant is sodium deoxycholate.

* * * * *

UNITED STATES PATENT AND TRADEMARK OFFICE
CERTIFICATE OF CORRECTION

PATENT NO. : 4 588 681
DATED : May 13, 1986
INVENTOR(S) : Takashi Sawada et al

It is certified that error appears in the above-identified patent and that said Letters Patent is hereby corrected as shown below:

Column 10, line 47; after "from" insert ---the---.
Column 11, line 21; change "adult cell" to ---adult T cell---.
Column 11, line 57; change "claim 13" to ---claim 12---.

Signed and Sealed this

Fourteenth Day of October, 1986

[SEAL]

Attest:

DONALD J. QUIGG

*Attesting Officer*  *Commissioner of Patents and Trademarks*